(12) United States Patent
Chiba et al.

(10) Patent No.: US 7,743,642 B2
(45) Date of Patent: Jun. 29, 2010

(54) MOISTURE ABSORBENT MATERIAL WITH INDICATOR FUNCTION, HUMIDITY INDICATOR AND PACKAGING BAG

(75) Inventors: Eisuke Chiba, Tokyo (JP); Tatsuya Ogawa, Tokyo (JP); Shinichi Koizumi, Tokyo (JP); Saori Takahashi, Tokyo (JP)

(73) Assignee: Kyodo Printing Co., Ltd., Tokyo (JP)

( * ) Notice: Subject to any disclaimer, the term of this patent is extended or adjusted under 35 U.S.C. 154(b) by 974 days.

(21) Appl. No.: 10/580,933

(22) PCT Filed: Nov. 26, 2004

(86) PCT No.: PCT/JP2004/017597

§ 371 (c)(1),
(2), (4) Date: May 30, 2006

(87) PCT Pub. No.: WO2005/053821

PCT Pub. Date: Jun. 16, 2005

(65) Prior Publication Data

US 2009/0013760 A1    Jan. 15, 2009

(30) Foreign Application Priority Data

Dec. 3, 2003   (JP)   ............................. 2003-404271
May 25, 2004  (JP)   ............................. 2004-154846

(51) Int. Cl.
G01N 5/02 (2006.01)
(52) U.S. Cl. .................................................... 73/29.04
(58) Field of Classification Search .................. 116/206; 73/29.04
See application file for complete search history.

(56) References Cited

U.S. PATENT DOCUMENTS

| 4,038,050 A | * | 7/1977 | Lowther ........................... 95/1 |
| 5,224,373 A |   | 7/1993 | Williams et al. |
| 5,712,023 A | * | 1/1998 | Nakajima et al. ........ 428/195.1 |

FOREIGN PATENT DOCUMENTS

| JP | 6-262028    | 9/1994  |
| JP | 2000-72977  | 3/2000  |
| JP | 2001-267064 | 9/2001  |
| JP | 2002-206046 | 7/2002  |
| JP | 2002-226715 | 8/2002  |
| JP | 2004-331855 | 11/2004 |

* cited by examiner

*Primary Examiner*—Hezron Williams
*Assistant Examiner*—Alex Devito (57) ABSTRACT

A moisture absorbent material (drying material) with an indicator function is provided without the use of cobalt chloride containing a heavy metal, low molecular organic substance and the like; and a humidity indicator permitting a state of humidity to be found in a simple manner is also provided. The moisture absorbent material with an indicator function (10) includes a resin layer (11) containing 5 to 80 wt % zeolite which is provided on at least one surface thereof with a printed layer including a character, shape, picture or the like, so that the printed layer may visibly appear due to the resin layer becoming transparent by moisture absorption. The humidity indicator (20) is formed by laminating a film (21) made of a zeolite-containing resin composition, a polyolefin film (22) having patterns (24) printed thereon that include characters, symbols, lines or the like, which are printed to have a difference in the print density, and an aluminum foil (26) through an adhesive, so that the patterns (24) may be made sequentially visible due to the film (21) made of the zeolite-containing resin composition becoming transparent by moisture absorption.

19 Claims, 7 Drawing Sheets

MOISTURE ABSORPTION (c)

MOISTURE ABSORBENT MATERIAL WITH INDICATOR FUNCTION, HUMIDITY INDICATOR AND PACKAGING BAG

TECHNICAL FIELD

The present invention relates to a moisture absorbent material with an indicator function that permits a pattern comprised of a character(s), shape, picture or the like to appear when absorbing moisture, a humidity indicator that allows a humidity state to be viewed due to changes in print density of characters or the like, and a packaging bag.

BACKGROUND ART

Conventionally, silica gel is known as a moisture absorbent material (drying material) furnished with an indicator function. The silica gel itself is a white material and is mixed with cobalt chloride to indicate a moisture absorbent state in a manner to show a blue color when dried and a pink color when absorbing humidity (moisture) in the atmosphere.

However, under the present situation, the twenty first century is said to be the century for preserving the environment and energy resources, and it is desirable to avoid use of heavy metals such as cobalt as much as possible in view of an environmental effect thereof. Therefore, the development of a material with an indicator function has been promoted in an effort to stop the use of cobalt.

For example, although a moisture absorbent function is not provided, a material with an indicator function is known which includes a pH indicator and an alkaline material to utilize a change in color due to evaporation of the alkaline material, for example (see patent documents 1 and 2).

A material is also known which includes a color-changeable pigment and an alkaline material to utilize a change in color due to oxygen or humidity in the atmosphere (see patent document 3).

A material is further known which includes a pigment and an organic solvent to utilize coloring due to volatilization of the organic solvent (see patent documents 4 and 5) or which utilizes a photochromic substance (see patent document 6).

The following invention is proposed for an environment determination indicator.

A temperature-indicating ink, a pH indicator, a photochromic ink or the like is used for a color-changing layer to correspond to environmental changes such as temperature, humidity, ultraviolet radiation amount, ammonia concentration, pH value, etc. Due to environmental changes, the color-changing layer changes from a certain color to a colorless one, or from a light color to a deep color, to thereby exhibit the indicator function (see patent document 7).

Patent document 8 describes a humidity indicator using a dye that absorbs moisture to change color.

Patent Document 1: Japanese Patent Application Laid-Open Publication No. 56-131684 (entire description)
Patent Document 2: Japanese Patent Application Laid-Open Publication No. 62-179640 (entire description)
Patent Document 3: Japanese Patent Application Laid-Open Publication No. 57-104884 (entire description)
Patent Document 4: Japanese Patent Application Laid-Open Publication No. 1-161081 (entire description)
Patent Document 5: Japanese Patent Application Laid-Open Publication No. 2-290591 (entire description)
Patent Document 6: Japanese Patent Publication No. 2-033385 (entire description)
Patent Document 7: Japanese Patent Application Laid-Open Publication No. 2003-192908 (entire description)
Patent Document 8: Japanese Utility Model Publication No. 5-15089 (entire description)

DISCLOSURE OF THE INVENTION

Problem to be Solved by the Invention

However, since each of these indicators includes a low-molecular organic substance, when formed at high temperature (150° C.-200° C.), these indicators are blackened or decomposed to cause performance deterioration. Toxicity is also problematic.

An object of the present invention is to provide a moisture absorbent material (drying material) furnished with an indicator function without the use of cobalt chloride containing a heavy metal, a low-molecular organic substance or the like, and a humidity indicator and a packaging bag which enable a state of humidity to be found in a simple manner.

Means for Solving Problem

In consideration of the above problems, the present invention employs the following means.

A moisture absorbent material with an indicator function is characterized in that the material comprises: a resin layer containing 5 to 80% zeolite by weight; and a printed layer including a character, shape, picture or the like and disposed on at least one side of the resin layer, so that the printed layer is made to visibly appear due to the resin layer becoming transparent by moisture absorption.

Since the resin layer absorbs moisture and changes from a whitish turbid state to a transparent state, the moisture absorbent material acts as an indicator indicating that the absorbent performance thereof has reached a limiting point.

The moisture absorbent material with an indicator function is characterized in that in addition, the printed layer is so formed that patterns constituted by characters, symbols, lines or the like have a difference in the print density thereof.

The moisture absorbent material with an indicator function is characterized in that in addition another resin layer containing 5 to 80% zeolite by weight is superposed on the side of the resin layer at which the printed layer is disposed.

The moisture absorbent material with an indicator function is characterized in that in addition the material has a barrier film superposed on at least one surface thereof.

The moisture absorbent material with an indicator function is characterized in that in addition an ink of one color selected from white, black, red, blue, green, yellow, indigo, cyan and magenta or an ink of mixed colors selected therefrom is applied between the barrier film and the printed layer.

The moisture absorbent material with an indicator function is characterized in that in addition an ink of one color selected from white, black, red, blue, green, yellow, indigo, cyan and magenta or an ink of mixed colors selected therefrom is applied to an opposite side of the resin layer which is provided with the printed layer.

The moisture absorbent material with an indicator function is characterized in that in addition the resin layer exhibits light transmittance of 70% or more when moisture absorption of the resin layer reaches a saturation state.

The moisture absorbent material with an indicator function is characterized in that in addition a film having a reflecting surface is superposed on at least one side of the moisture absorbent material.

The moisture absorbent material with an indicator function is characterized in that in addition an ink used for the printed layer has a weight ratio of pigment or dye to resin within a range of 0.05 to 50 wt %.

The moisture absorbent material with an indicator function is characterized in that in addition the printed layer has an ink film thickness of 0.3 to 100 μm.

The moisture absorbent material with an indicator function is characterized in that in addition the material is so constructed that a printed pattern appears when a difference in optical density values between a whitish turbid state and a transparent state of the resin layer is rendered 0.05 or more.

A humidity indicator is characterized in that a film using a zeolite-containing resin composition, a polyolefin film having a pattern printed thereon, and a film having a reflecting surface are laminated on one another, so that the pattern is rendered visible by utilizing a change of the film using the zeolite-containing resin composition from a whitish turbid state to a transparent state due to moisture absorption.

The humidity indicator is characterized in that in addition a thermoplastic resin is superposed on the film using the zeolite-containing resin composition so as to regulate the rate of moisture absorption, to thereby control an increase rate of visibility of the pattern.

The humidity indicator is characterized in that in addition a paint for enlarging an angle of visibility is applied to a surface of the thermoplastic resin.

The humidity indicator is characterized in that in addition a film having a low refractive index is interposed between the polyolefin film having the pattern printed thereon and the film having the reflecting surface.

The humidity indicator is characterized in that in addition a laminate constituted of the film using the zeolite-containing resin composition, the polyolefin film having the pattern printed thereon and the film having the reflecting surface is entirely interposed between films having a width larger than that of the film using the zeolite-containing resin composition and then subjected to a heat lamination process.

The humidity indicator is characterized in that in addition the films used for the heat lamination have a water vapor transmission rate ranging from 0.1 to 100 $g/m^2/day$.

The humidity indicator is characterized in that in addition a color sample is printed on a film layer of the films used for the heat lamination so as to judge a state of the pattern which appears with moisture absorption.

The humidity indicator is characterized in that in addition the pattern is formed to have a difference in the print density of characters, symbols, lines or the like so that the degree of visibility may change, whereby the humidity of a space is clearly indicated.

A packaging bag is characterized in that the bag is formed in a bag shape using a film provided on the whole of or on part of a face thereof with a zeolite-containing resin layer.

EFFECT OF THE INVENTION

According to the present invention, an environmentally-friendly moisture absorbent material with an indicator function that eliminates the use of cobalt can be provided. Since the color changing layer described in the background art statement is not required to be inserted as an individual layer and only the pattern is printed, the product cost can be reduced. The relationship between the optical density of appearing characters and the moisture absorption enables the moisture absorption capacity of the moisture absorbent material to be checked without opening a packaging bag.

The superposition of various films such as polyolefin or the like on the zeolite-containing film enables the time until saturation to be controlled on the basis of the thicknesses of the former. The moisture absorption can be adjusted by changing the thickness of the zeolite-containing resin layer.

The patterns corresponding to moisture absorption levels can be viewed sequentially depending on the degree of clearing of the film due to moisture absorption, so that the moisture absorption state can be known at an intermediate stage.

Humidity of an article stored in the packaging bag can be absorbed, to thereby place the article in a suitably dry condition.

BRIEF DESCRIPTION OF DRAWINGS

FIGS. 2(a) to 2(c) are views showing another embodiment of a moisture absorbent material with an indicator function according to the present invention, wherein

BEST MODE FOR CARRYING OUT THE INVENTION

Figure 1:
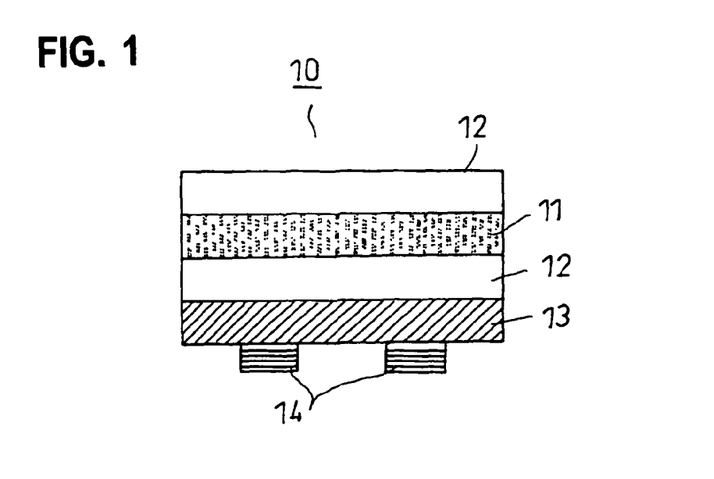
FIG. 1 is a cross-sectional view of an embodiment of a moisture absorbent material with an indicator function according to the present invention.

FIG. 1 shows an embodiment of a moisture absorbent material with an indicator function according to the present invention.

As shown in FIG. 1, a moisture absorbent material with an indicator function 10 includes a zeolite film 11 formed from a zeolite-containing organic resin composition, wherein when the film 11 is formed, polyolefin (e.g., LLDPE) 12, 12 is superposed on the both sides thereof by co-extrusion, and polyester (PET in this embodiment) acting as a barrier film 13 is overlaid on one polyolefin surface. A pattern 14 constituted of a character or characters, a shape or shapes, a picture or the like is printed on a surface of the barrier film 13.

The zeolite film 11 is manufactured as follows.

First, a base resin is mixed with 5 to 80% of zeolite and formed into a film shape after adding an additive, such as an ethylene-acrylic ester-maleic anhydride copolymer or the like, at a mixture ratio of 1 to 20% to enhance an affinity therebetween. The mixture ratio of zeolite is preferably about 40 to 80% by weight and is more preferably about 50 to 80% by weight.

As the base resin, one or more resins are selected from LDPE (low density polyethylene), LLDPE (linear low density polyethylene), PP (polypropylene), and various copolymers, for example, ionomers, EAA, EMAA, EVA, EEA, EMA, EMMA, etc. and are used alone or in a mixture form. Such resins used for the base resin are suitably selected from these resins so as to include one or ones having a high MFR (melt flow rate), and preferably, an MFR of 10 (g/10 minutes) or more as measured under the conditions of a temperature at 190° C. and load of 21.18 N.

Zeolite is an inorganic porous substance with a pore size from 3 to 10 Å and used as a preferable absorbent. Zeolite having the average particle diameter of, for example about 10 μm, is preferably used.

Zeolite is a porous granular substance with polarity that is used for separating substances depending on a size of a molecule and has a structure with uniform fine pores, so that zeolite absorbs small molecules that can enter cavities of the fine pores to act as a kind of sieve.

When the zeolite film 11 thus formed absorbs moisture and is saturated, the film 11 changes from a whitish turbid state to a transparent state. Therefore, in a case where a pattern is printed on the backside of the film 11 opposite from a side to be viewed, the pattern can be viewed when the film 11 absorbs moisture.

In a case where another zeolite film is further superposed on the side of the zeolite film 11 that has the printed layer disposed thereon to thereby arrange the zeolite films on both sides of the printed layer, the printed layer cannot be viewed from either side when the zeolite films are in an opaque state. Accordingly, such a construction is particularly useful when used for a humidity indicator that can be checked from both sides.

When only the zeolite film is used, since the resin and the zeolite are mixed and thus the film surface is rough, the zeolite film has a low light transmittance. In addition, when only the zeolite film is used, as the zeolite film very quickly absorbs moisture in the atmosphere, it is difficult to control the time until saturation; and the film strength is reduced.

Therefore, superposition of a film of a material such as polyolefin 12 can enhance the strength of the entire film, reduce the roughness of the film surface, restrain falling of the zeolite crystal aggregate, and facilitate clearing of the zeolite film or making it become transparent due to the moisture absorption. The superposition of the film also enables the rate of moisture absorption to be controlled by selecting a material for the film and a thickness of the film. The polyolefin 12 used in this case is transparent.

As the resin to be superposed, LDPE (low density polyethylene), LLDPE (linear low density polyethylene), PP (polypropylene), PS (polystyrene), PMMA (polymethyl methacrylate), nylon, polyester (PET, PBT, PEN), PAN (polyacrylonitrile), and various copolymers, such as ionomer, EAA, EMAA, EVA, EVOH, EEA, EMA and EMMA are used. Fluorocarbon resins such as PTEE can also be used.

Since polyester constituting the barrier film 13 has a barrier to permeation of moisture, the moisture absorption from one or both sides of the zeolite film can further be controlled by affixing the barrier film or films.

A barrier layer is preferably formed of a gas barrier film, for example, an aluminum laminate film, an aluminum-evaporated film, an inorganic oxide-evaporated film, a K-coated film (film having vinylidene chloride-vinyl chloride copolymer latex applied thereto), an OPP film (biaxially oriented polypropylene film), an OPE film (oriented polyethylene film) or the like.

The barrier layer can be made of a coextruded film, an engineering plastic film such as polyimide, polycarbonate, PPS (polyphenylene sulfide) or PES (polyether sulfide), a fluorocarbon resin film such as PTFE, or the like.

The use of the barrier film enables the time until saturation of the film to be controlled from one day to 100 days or more, for example. The lamination of the barrier film on the polyolefin film advantageously enhances the clearness.

With regard to an ink used for printing the pattern 14, it is preferred that the weight ratio of a pigment or dye to resin be 0.05 to 50 wt % and a film thickness thereof be 0.3 to 100 μm.

A reflective layer may be provided using a reflective metal foil or a metal evaporated layer, such as an aluminum foil, an aluminum-evaporated layer, a tin foil, a tin-evaporated layer, a nickel foil or the like.

Although the pattern 14 is printed on the outer surface of the barrier film 13 in the embodiment described above, the pattern 14 may be printed on the surface of the polyolefin 12 superposed on the side of the zeolite film 11 opposite from the barrier film 13. For example, in the case of a packaging bag storing inside food that absorbs moisture, the barrier film 13 needs to be disposed on the outer side to prevent the moisture in the atmosphere from infiltrating inside.

Although the film portion of the moisture absorbent material with an indicator function 10 is constituted by the zeolite film 11 formed from the zeolite-containing organic resin composition, the polyolefin (LLDPE) 12, 12 superposed on both sides of the film 11 by coextrusion when the film 11 is formed and polyester (PET in this example) serving as the barrier film 13 laminated on one polyolefin surface in the embodiment described above, many other layer configurations may be used. For example, only the zeolite film 11 may be used under certain circumstances as shown in FIG. 3(a).

Figure 3:
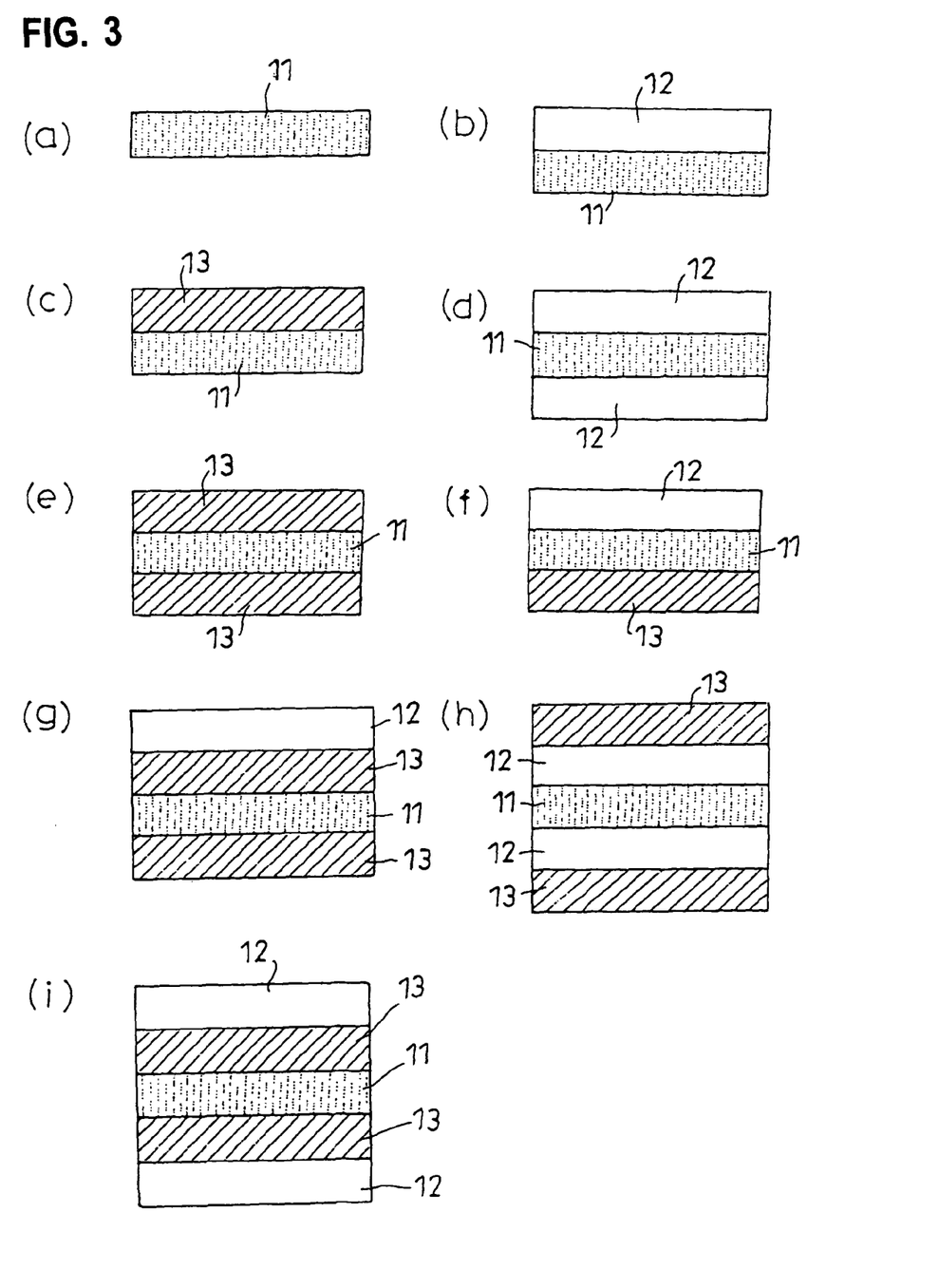
FIGS. 3(a) to 3(i) are views of variations of a film portion in the moisture absorbent material with an indicator function according to the present invention.

As shown in FIG. 3(b), the polyolefin 12 may be superposed on only one side of the zeolite film 11, and as shown in FIG. 3(c), the polyester 13 may be superposed on only one side of the zeolite film 11.

As shown in FIG. 3(d), the polyolefin 12 may be superposed on both sides of the zeolite film 11, and as shown in FIG. 3(e), the polyester 13 may be superposed on both sides of the zeolite film 11.

As shown in FIG. 3(f), the polyolefin 12 and the polyester 13 may be superposed on one side and the other side of the zeolite film 11, respectively, and as shown in FIG. 3(g), the polyester 13 may be superposed on both sides of the zeolite film 11 with the polyolefin 12 further superposed only on the polyester 13 on one side.

As shown in FIG. 3(h), the polyolefin 12 may be superposed on both sides of the zeolite film 11 with the polyester 13 further superposed on both sides thereof, and as shown in FIG. 3(i), the polyester 13 may be superposed on both sides of the zeolite film 11 with the polyolefin 12 further superposed on both sides thereof.

The layer configurations of the thermoplastic resin and the barrier film superposed on the zeolite film are not limited to the above configurations.

Whichever film is used, the pattern 14 used as an indicator is normally printed on the backside of the zeolite film 11 opposite from a side to be viewed. However, when the color of the pattern 14 is made the same as the turbid color of the zeolite film 11, the pattern 14 may be printed on the front side of the zeolite film 11 as viewed from said side. When the zeolite film 11 is in the whitish turbid state, the pattern 14 merges with the background color and cannot be distinguished, and when the zeolite film 11 becomes transparent, the pattern 14 visibly appears.

The printed layer may be disposed at any site in the laminate film depending on the purpose or usage.

Figure 2:
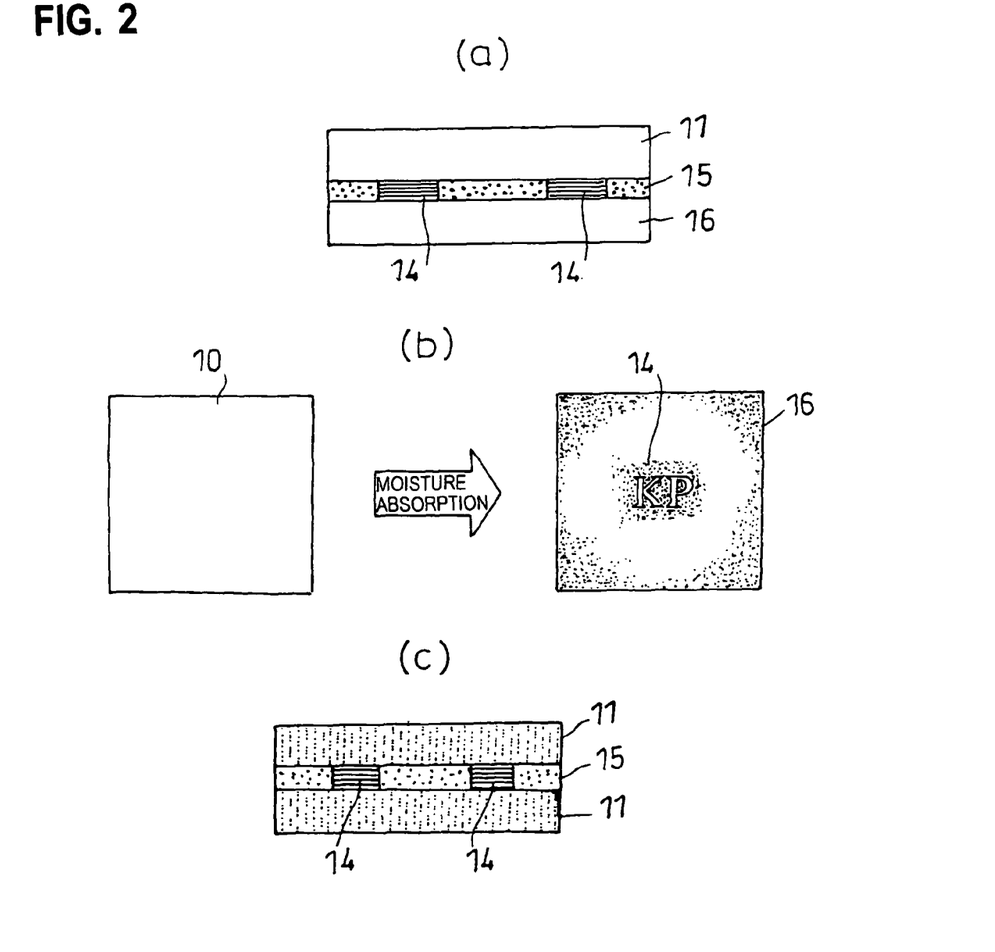
FIG. 2(a) is a cross-sectional view of the moisture absorbent material.
FIG. 2(b) is an explanatory illustration showing the function of the moisture absorbent material.
FIG. 2(c) is a cross-sectional view of another example of the moisture absorbent material.

In a case where it is difficult to view the pattern 14 when moisture absorption of the zeolite film 11 comes into a saturation state, an aluminum (Al) foil 16 is affixed to the surface of the moisture absorbent material with an indicator function 10 which has the pattern 14 printed thereon through an adhesive 15 as shown in FIG. 2(a), to thereby increase the reflectivity and enhance the turbid state.

As shown in FIG. 2(b), the zeolite film 11 looks white as it is turbid before absorbing moisture, whereas the zeolite film 11 becomes transparent when absorbing moisture, so that the pattern 14 (characters "KP" in FIG. 2(b)) which emerges in the reflected light from aluminum can be viewed.

As shown in FIG. 2(c), the zeolite films 11 are superposed on both sides of the pattern 14 printed surface, to thereby provide a suitable construction enabling the pattern 14 to be viewed from both front and back sides.

In such cases, it is difficult to form a packaging bag for absorbing moisture to dry a material stored inside. This is because the inside of the bag cannot be viewed. Therefore, in one way, the moisture absorbent material with an indicator function 10 which is formed into a sheet is placed in a transparent bag along with the material that is the target of the moisture absorption and drying, and is permitted to be viewed from the outside.

An ink of one color selected from white, black, red, blue, green, yellow, indigo, cyan and magenta or an ink of mixed colors selected therefrom may be applied between the barrier film layer (polyester) 13 and the printed layer so as to color the pattern 14 viewed when the indicator function is performed.

Alternatively, an ink of one color selected from white, black, red, blue, green, yellow, indigo, cyan and magenta or an ink of mixed colors selected therefrom may be applied to an opposite side of the resin layer provided with the printed layer to enhance the visibility of the pattern 14 viewed when the function is performed.

Although a monochromatic indicator is limited in visibility since the range of absorption wavelengths is limited, the range of absorption wavelengths can be extended by mixing some of the above colors arbitrarily, to thereby enhance visibility.

Even when the zeolite film 11 described above is formed at a temperature at which low-molecular organic matter degrades, the indicator function is not deteriorated.

EXAMPLE 1

A. A moisture absorption test was performed for the film portion of the moisture absorbent material with an indicator function 10.

The film had a configuration shown in FIG. 1, wherein a thickness of the zeolite film 11 (50 wt % of zeolite with a 3 Å pore size (molecular sieve 3A) and 50 wt % of LDPE) was 130 μm; a thickness of both thermoplastic resin layers (LLDPE) 12 was 10 μm; and a thickness of the barrier film (PET) 13 was 25 μm. The moisture absorption and transmittance of visible light due to clearing of the zeolite film were measured as the time elapsed. The test was performed at 25° C. and relative humidity of 20%. The result is shown in Table 1. When the moisture absorption of the film exceeds 18%, the transmittance of visible light exceeds 70% and the clearing of the film becomes prominent.

In this case, a formula for calculating the moisture absorption is as follows:

(Increase of moisture/amount of zeolite in film)×100.

In this formula:

Increase of moisture=film weight at the time of measurement−film weight at measurement start time; and amount of zeolite in film=initial film weight−resin weight.

TABLE 1

Moisture Absorption Test

| | Moisture Absorption (%) | Transmittance (%) | State of Film |
|---|---|---|---|
| Immediately after Experiment Start | 0 | 30 | Whitish Turbid |
| After 3 Days | 12.0 | 60 | Whitish Turbid |
| After 6 Days | 18.8 | 70 | Clearing of Film Becomes Prominent. |
| After 8 Days | 21.5 | 80 | Film is Saturated. |

B. An indicator test was performed.

A material having a configuration shown in FIG. 2(a) was used, wherein a film portion thereof included only a zeolite film 11 (50 wt % of zeolite with a 3 Å pore size (molecular sieve 3A) and 50 wt % of LDPE). A pattern 14 was printed directly onto the zeolite film 11, and an adhesive was applied to affix an aluminum (Al) foil 16 serving as a film with a reflecting surface. The ink used for printing the pattern had a weight ratio of pigment or dye to resin which was 0.05 to 50 wt % and the film thickness thereof was in the range of 0.3 to 100 μm. The result is shown in Table 2. Table 2 shows the result obtained when the weight ratio of the pigment was 1 wt % and the film thickness was 5 μm.

Since the aluminum foil was affixed to the under side of the moisture absorbent film, the light reflectivity was increased, whereby the appearance of the printed pattern due to the clearing was enhanced. The experiments were performed for white, yellow, magenta, cyan and black, and the appearing time of each pattern was measured. Table 2 shows the result of the indicator test for the white pattern.

The moisture absorption took place only in a direction from the top surface of the film.

Although the time until saturation varies depending on a test environment, the moisture absorption required for the pattern appearing is substantially identical in each test environment.

Although the appearing time of the indicator is different from the elapsed time shown in Table 1, the moisture absorption is substantially the same as the moisture absorption shown in Table 1.

TABLE 2

| | Indicator Test | |
|---|---|---|
| Test Environment | 23° C., 50% RH | 25° C., 20% RH |
| Elapsed Days until Pattern Appearing | 5 Days | 8 Days |
| Moisture Absorption | 17.8% | 17.4% |

C. An optical density numeric conversion test was performed for a printed pattern.

A film had a configuration shown in FIG. 1, wherein a thickness of a zeolite film 11 (50 wt % of zeolite with a 3 Å pore size (molecular sieve 3A) and 50 wt % of LDPE) was 60 μm, a thickness of both thermoplastic resin layers was 20 μm, and a thickness of PET was 25 μm. A printed pattern was white.

In the test environment, a temperature was 23° C. and a relative humidity was 50%. The result is shown in Table 3.

A measuring instrument was Macbeth RD918.

The film became transparent on the fourth day. That is, in such a configuration, the printed pattern appears when a difference in optical density values is 0.05 or more between the whitish turbid state and the transparent state of the film.

TABLE 3

| | Optical Density Numeric Conversion Test | | |
|---|---|---|---|
| | Density of Pattern | Density of Background | Pattern Appearing |
| First Day | 0.18 | 0.18 | x |
| Second Day | 0.20 | 0.20 | x |
| Third Day | 0.23 | 0.21 | x |
| Fifth Day | 0.27 | 0.22 | ○ |
| Sixth Day | 0.31 | 0.22 | ○ |

The densities of the pattern and the background are those of respective parts indicated by reference numerals 14 and 16 in FIG. 2(b).
Note:
A symbol "x" indicates that the pattern cannot be viewed since the film is in the turbid state and a symbol "○" indicates that the pattern can be viewed since the film is in the transparent state.

Now, an embodiment of a humidity indicator according to the present invention will be described hereinafter.

Figure 4:
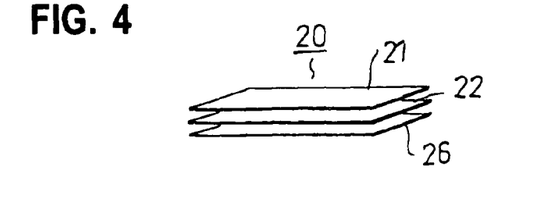
FIG. 4 is an illustration showing an embodiment of a humidity indicator according to the present invention.

As shown in FIG. 4, a humidity indicator 20 is formed by laminating a film 21 using a zeolite-containing resin composition, a polyolefin film 22 having a pattern printed thereon and an aluminum foil 26 by the use of an adhesive. The film 21 using the zeolite-containing resin composition (50 wt % of zeolite with a 3 Å pore size (molecular sieve 3A) and 50 wt % of LDPE) has a thickness of 130 μm, the polyolefin film (LLDPE) 22 has a thickness of 10 μm, and the aluminum foil has a thickness of 9 μm.

The film 21 made of the zeolite-containing resin composition has the same quality as the zeolite film 11 described in the above embodiment of the moisture absorbent material with an indicator function 10. The polyolefin film 22 has the same quality as the polyolefin film 12 described in the above embodiment. The aluminum foil 26 may be replaced by an aluminum laminate film or an aluminum evaporated film.

Figure 5:
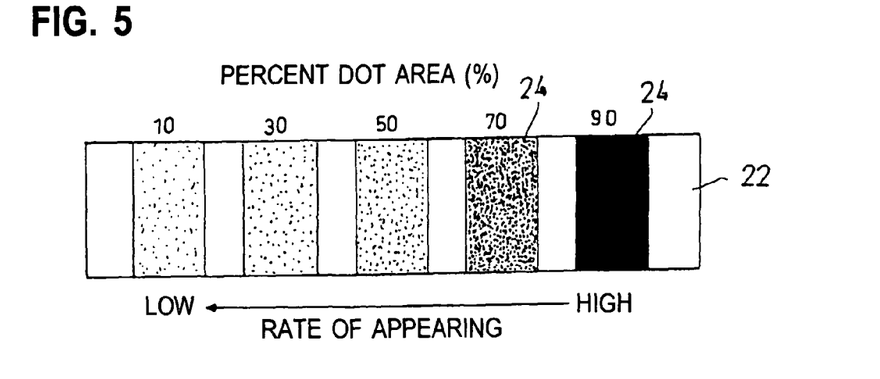
FIG. 5 is a view of a pattern used in the humidity indicator shown in FIG. 4.

With regard to patterns 24 printed on the polyolefin film 22, for example, as shown in FIG. 5, the film 22 is formed in a strip shape, and rectangular patterns having 90, 70, 50, 30 and 10 dot-area percentages are sequentially printed orthogonal to a longitudinal direction of the film face. In this case, the film 22 is transparent and halftone dots are white dots. In FIG. 5, the darker the pattern is depicted in a black color, the higher the percent dot area of the pattern formed by white halftone dots is.

When the film 21 absorbs moisture and changes gradually from the whitish turbid state to the transparent state, the pattern having the highest percent dot area can be first viewed before a background of the aluminum foil 26. As moisture absorption of the film 21 progresses, the patterns having the lower dot-area percentages can be viewed sequentially.

Figure 6:
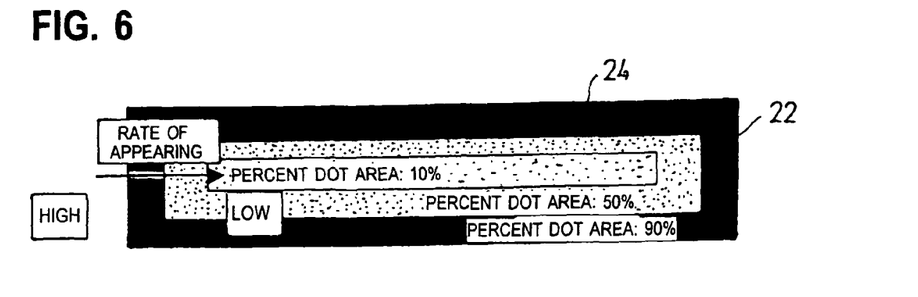
FIG. 6 is a view of another pattern used in the humidity indicator shown in FIG. 4.

In another example shown in FIG. 6, patterns 24 may be arranged in such a manner that a pattern having a high percent dot area is printed at an outer edge of a strip-shaped film 22, and patterns having lower dot-area percentages are printed in order toward the center of the film. This pattern arrangement is formed in consideration of the fact that the moisture absorbent film 21 absorbs moisture from end faces thereof and is saturated faster at an end portion thereof.

Figure 7:
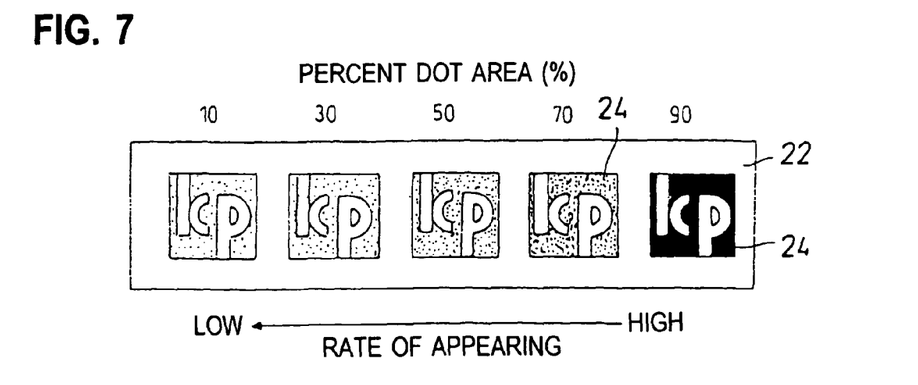
FIG. 7 is a view of yet another pattern used in the humidity indicator shown in FIG. 4.

In yet another example shown in FIG. 7, patterns 24 including characters or numerals may be printed at different dot-area percentages and clearing of the film 21 may be utilized to display a numeric value for each degree of humidity as the film gradually becomes transparent. Although the characters are "kp" in FIG. 7, for example, numerals "40", "45", "50", "55" and "60" may be printed at 90, 70, 50, 30 and 10 dot-area percentages, respectively, and when the pattern of the numeral "40" of a 90 percent dot area is viewed, it may be known that humidity is 40% in a bag which has the film disposed therein.

EXAMPLE 2

D. Indicator Appearing Test

In a bag made of a transparent film (LLDPE/PET), 10 g of silica gel and a humidity indicator 20 with patterns 24 described above [a film using a zeolite-containing resin composition 21 (50 wt % of zeolite with a 3 Å pore size (molecular sieve 3A) and 50 wt % of LDPE) with a thickness of 130 μm, a polyolefin film (LLDPE) 22 with a thickness of 10 μm and an aluminum foil 26 with a thickness of 9 μm] were contained, and changes in humidity and visibility of the patterns in the bag were measured. In the outside environment, the temperature was 25° C. and humidity was 50%. The result shown in FIG. 8 was obtained.

Figure 8:
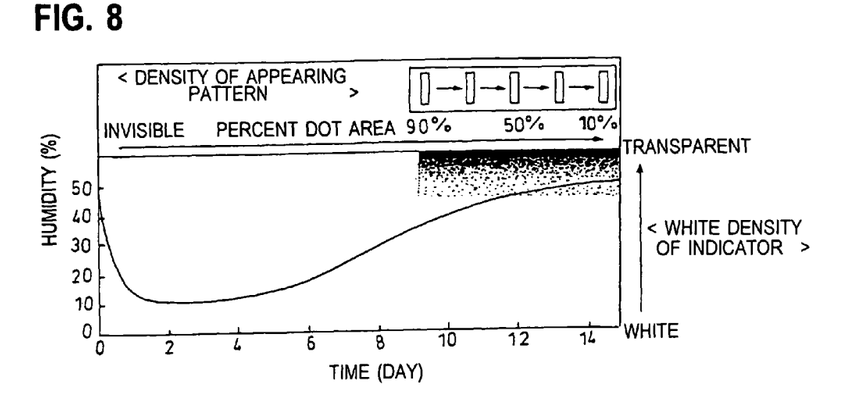
FIG. 8 is a diagram showing an indicator appearing test using different dot-area percentages and changes in humidity.

When humidity rose to near 40%, the pattern of the indicator could be viewed (printed layer in this case: 50% pigment, a 90 percent dot area). The indicator can be made to appear at an arbitrary humidity by changing the thickness of the moisture absorbent film 21, zeolite content, pattern density or the like.

Figure 9:
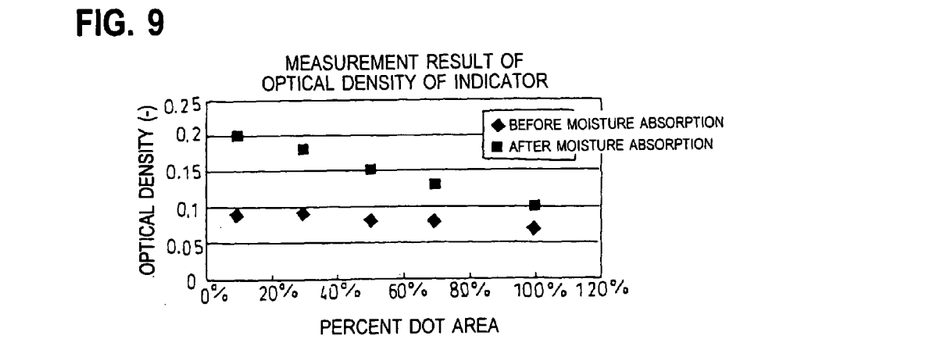
FIG. 9 is a diagram showing differences in optical densities between before and after moisture absorption of a film.

In the patterns of FIGS. 5, 6, and 7, differences in optical densities of the patterns are changed between before and after the moisture absorption of the film. Such states are shown in FIG. 9. As a result, a state of humidity can be checked from the difference in optical density between the pattern and the background.

Although the patterns are formed by the white dots in the above embodiment of the humidity indicator, the pattern may be formed by dots of any one of black, red, yellow, blue, etc., or the pattern may be printed using dots of a mixture of above colors. A synthetic resin film itself which is colored may be used together.

Figure 10:
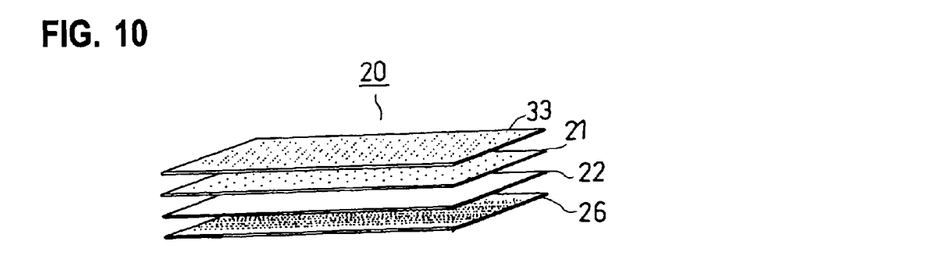
FIG. 10 is an illustration of an example in which thermoplastic resin is superposed on a moisture absorbent film of the humidity indicator shown in FIG. 4.

Although the humidity indicator 20 is formed by laminating the film 21 made of the zeolite-containing resin composition, the polyolefin film 22 having the pattern printed thereon and the aluminum foil 26 by the use of an adhesive as shown in FIG. 4, a thermoplastic resin 33 may be superposed on the film 21 made of the zeolite-containing resin composition as shown in FIG. 10.

The thermoplastic resin 33 includes PET, LLDPE, LDPE, HDPE, nylon, EVA, PP, ionomer, polystyrene, PVC, EVOH, cellophane, etc.

EXAMPLE 3

Figure 11:
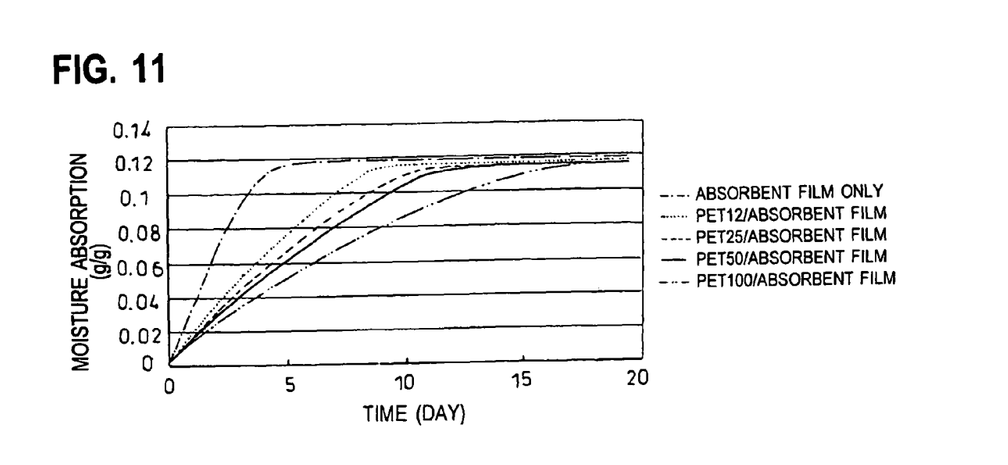
FIG. 11 is a diagram showing moisture absorption states of the moisture absorbent film, which are measured with respect to different thicknesses of the thermoplastic resin of the humidity indicator shown in FIG. 10.

The humidity indicators having a configuration shown in FIG. 10 and utilizing PET as the thermoplastic resin 33 were used to compare the rate of moisture absorption thereof with a sample having a moisture absorbent film only. The result is shown in FIG. 11. In the environment, the temperature was 25° C. and humidity was 50%. PET was TOYOBO E5100 (manufactured by Toyobo Co., Ltd.) and the thickness was changed to be 12, 25, 50 and 100 μm in the experiment.

As a result, it is found out that the rate of moisture absorption of the zeolite-containing resin layer can be reduced by superposing PET on the moisture absorbent film. It is also found out that the rate of moisture absorption is reduced by increasing the thickness of PET. That is, it is indicated that the visibility of the printed pattern appearing after the moisture absorption can be controlled by superposing the thermoplastic resin such as PET on the moisture absorbent film. Therefore, the retention period of the indicator can be controlled by superposing such a thermoplastic resin on the moisture absorbent film.

EXAMPLE 4

The rate of visibility of the indicator was then observed.

Figure 12:
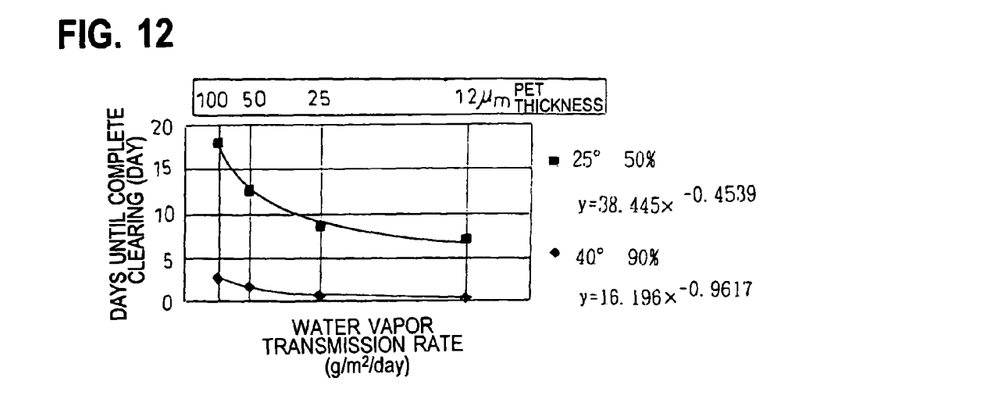
FIG. 12 is a diagram showing the number of days until the moisture absorbent film completely clears, which is measured with respect to different thicknesses of the thermoplastic resin.

Each sample formed by superposing PET on the moisture absorbent film was stored in an environment at a temperature of 25° C. and humidity of 50% and in an environment at a temperature of 40° C. and humidity of 90% to observe visibility (days until the film completely clears). The result is shown in FIG. 12.

Since a water vapor transmission rate (g/m$^2$/day) varies depending on the thickness of PET, each equation is indicated as a function of the water vapor transmission rate and the days until the film completely clears.

Figure 13:
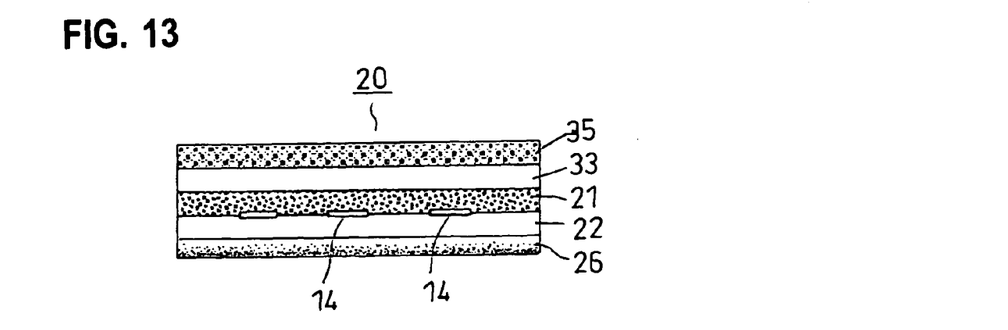
FIG. 13 is a view showing a state in which an antireflective layer with a low refractive index is applied to the surface of the humidity indicator shown in FIG. 10.

In the case of the humidity indicator 20 shown in FIG. 10, when an angle of visibility is changed, it may be difficult to view the change of state due to the light reflection on the surface. Therefore, as shown in FIG. 13, a layer of a low refractive index is formed as a surface layer 35 which is comprised of a resin containing 15 to 30% of glass beads by coating. In this way, the surface reflection of light from a fluorescent lamp or the like can be restrained to provide the humidity indicator 20 with an enlarged angle of visibility and enhanced visibility.

EXAMPLE 5

A paint for forming the layer of a low refractive index is an acrylic UV cure resin containing glass beads, and the result obtained when changing the bead content to observe the visibility of the indicator is shown in Table 4.

TABLE 4

| Relationship between Bead Content and Visibility | | | | |
|---|---|---|---|---|
| Bead Content (wt %) | 7.5 | 10 | 15 | 25 |
| Visibility | x | x | ○ | ○ |

○: improved
x: not improved

It is confirmed that the visibility of the indictor after coating is affected by the content of the glass beads.

Figure 14:
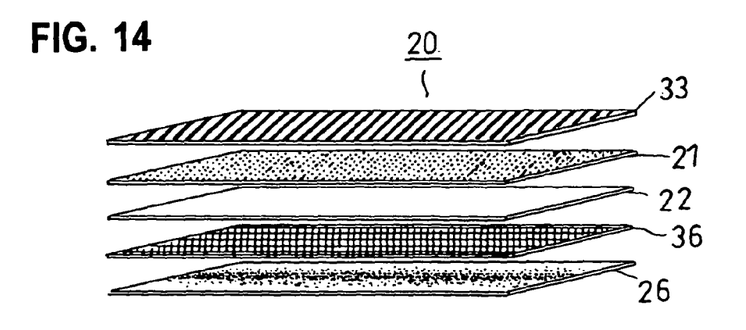
FIG. 14 is a view showing a state in which a low refractive index layer is interposed between a resin layer having a pattern printed thereon and a reflective film.

To improve the visibility of the indicator, in the configuration shown in FIG. 10, a film of a low refractive index 36 may be interposed between the aluminum foil 26 and the pattern printed layer 22 as shown in FIG. 14.

Figure 15:
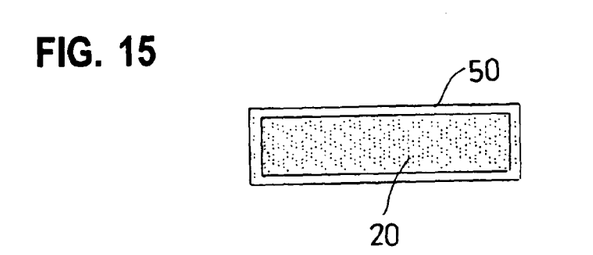
FIG. 15 is an illustration showing a state in which the entire humidity indicator is covered with a heat-lamination film.

Since the humidity indicator 20 tends to absorb moisture from side surfaces, the moisture absorption rate can be controlled by performing a process of wrapping the entire humidity indicator 20 with a heat lamination film or films 50 which is/are wider than the humidity indicator 20. The heat lamination film may be constituted by affixing LLDPE, LDPE or HDPE to thermoplastic resin such as PET, nylon, EVA, PP, ionomer, polystyrene, PVC, EVOH, cellophane or the like.

EXAMPLE 6

Experiment on Rate of Moisture Absorption

Figure 16:
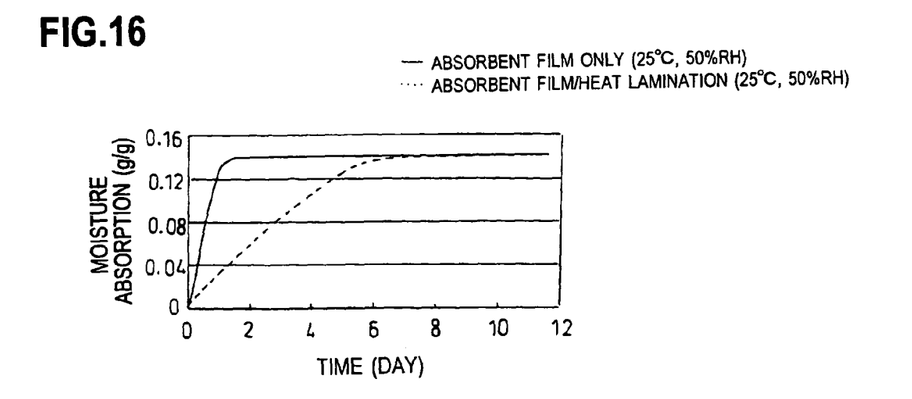
FIG. 16 is a diagram showing changing states of moisture absorption measured with respect to the moisture absorbent film only and with respect to the moisture absorbent film with a heat-lamination film.

A moisture absorbent film alone and a moisture absorbent film with a heat lamination film were stored in an environment at 25° C. and 50% RH to measure moisture absorption (g/g). The result is shown in FIG. 16. The water vapor transmission rate of the utilized heat lamination film was 5.9 (g/m$^2$/day).

As shown in FIG. 16, the time until the saturation of the moisture absorbent film can be changed by the heat lamination film, and therefore, the rate of moisture absorption can be controlled by the heat lamination film. The humidity indicator with no heat lamination film absorbs moisture mainly from the side surfaces and becomes transparent gradually from edges toward the center thereof. However, it is confirmed in the above configuration that the entire surface of the indicator becomes transparent and that the visibility of the pattern is changed gradually.

In the humidity indicator 20 using the film 21 made of the zeolite-containing resin composition, the moisture absorption state is judged when the humidity indicator is changed from the turbid state to the transparent state to render the character pattern of the humidity indicator 20 visible. Since the judgment criterion may vary with each individual, the following configuration is advantageous.

Figure 17:
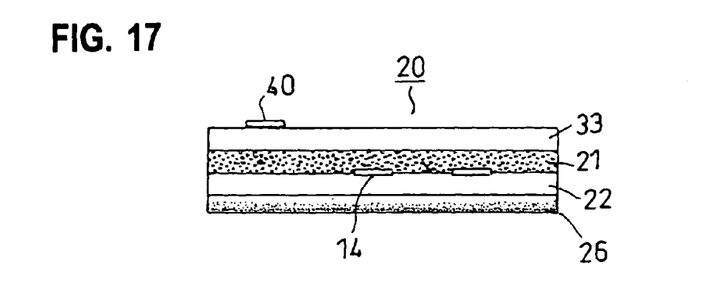
FIG. 17 is a view of an example in which a judgment color of the same color as that of the pattern is printed on the top surface of the humidity indicator.
Figure 18:
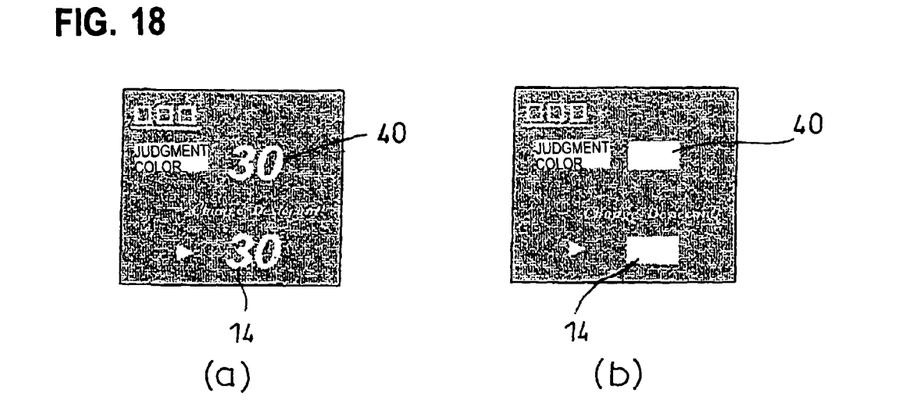
FIGS. 18(a) and 18(b) are views each showing a state of the humidity indicator shown in FIG. 17 which has completely absorbed moisture.

More particularly, as shown in FIG. 17, a judgment color printed portion 40 corresponding to the moisture absorption state of the film is disposed on the front side of the humidity indicator 20 to be viewed. Since the moisture absorption state can be judged by comparing the density of the judgment color with the density of the character pattern 14 that becomes visible, an individual difference can be restrained at the time of the judgment. FIGS. 18(a) and 18(b) each show the result thereof. The words "judgment color" printed in the vicinity of the judgment color printed portion 40 facilitate clarifying the target of the judgment. In FIG. 18(a), the characters of the judgment color printed portion 40 are "30" and the pattern 14 is constituted by characters "30" as well. In FIG. 18(b), the judgment color printed portion 40 is indicated by a density and the pattern 14 is also indicated by a density.

Figure 19:
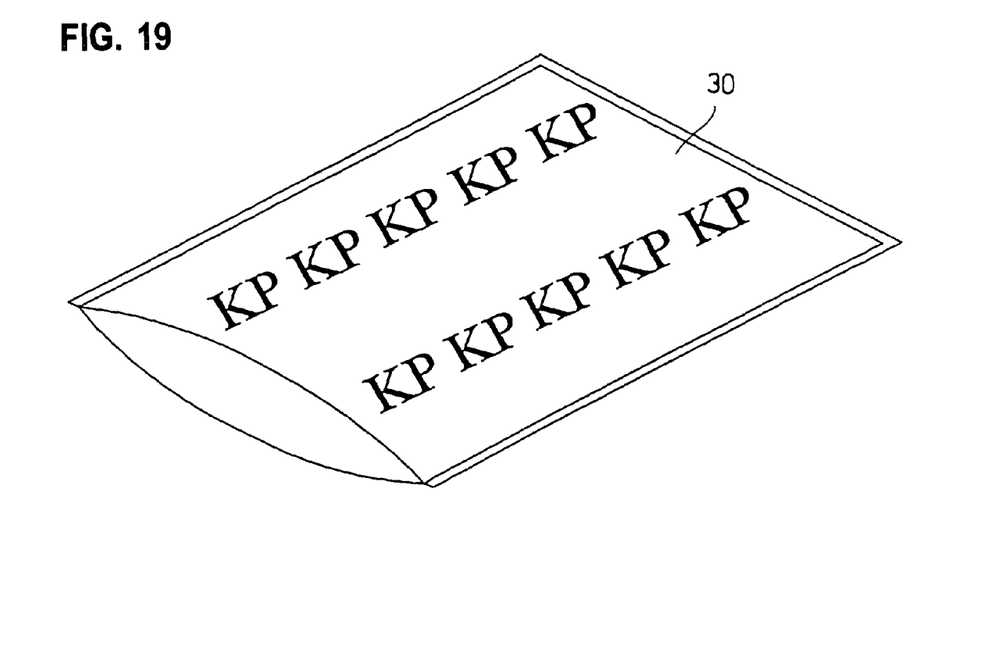
FIG. 19 is an illustration showing a packaging bag formed of a film which is provided entirely or partially on the face thereof with a zeolite-containing resin layer.

FIG. 19 shows a packaging bag 30 that is a bag formed using a film provided entirely or partially on the face thereof with a zeolite-containing resin layer having a humidity indicator function. This bag can keep an article or articles stored therein in a suitable dry condition.

The bag is constructed by lamination of the zeolite film and the printed layer while the zeolite film is disposed at the outer side of the bag, so that the pattern printed inside can be viewed as the bag becomes transparent. When the bag is formed, a heat seal layer is overlaid on the inside, whereby a three-side sealed bag, a four-side sealed bag, a gadget bag or the like can be formed. In the case of the four-side sealed bag, a film including a reflective layer can be laminated with a film not including a reflective layer.

INDUSTRIAL APPLICABILITY

The moisture absorbent material with an indicator function according to the present invention which is formed into a film shape can be utilized as a functional packaging material or a packaging bag with a drying agent (moisture absorbent material) for electronic components, food, drugs, or the like. The moisture absorbent material of the present invention is not limited to these applications. In the humidity indicator according to the present invention, the patterns corresponding to the moisture absorption levels can be sequentially viewed depending on the degree of transparency of the film, and thus the humidity indicator is suitable for placing in a food packaging bag or the like so as to enable the inside humidity situation to be comprehended.

EXPLANATIONS OF REFERENCE NUMERALS

10: Moisture absorbent material with indicator function
11: Zeolite film
12: Thermoplastic resin
13: Barrier film
14: Pattern
15: Adhesive
16: Aluminum foil
20: Humidity indicator
21: Film using zeolite-containing resin composition
22: Polyolefin film
24: Pattern
26: Aluminum foil
30: Packaging bag
33: Thermoplastic resin (PET)
35: Surface layer (layer of low refractive index)
36: Film of low refractive index
40: Judgment color printed portion

The invention claimed is:

1. A moisture absorbent material with an indicator function, characterized in that the material comprises: a resin layer containing 5 to 80% zeolite by weight; and a printed layer including a character, shape, picture or the like and disposed on at least one side of said resin layer, so that said printed layer is made to visibly appear due to said resin layer becoming transparent by moisture absorption, wherein said printed layer is so formed that patterns constituted by characters, symbols, lines or the like have a difference in the print density relative to the resin layer to appear visible when the resin layer becomes transparent by moisture absorption.

2. The moisture absorbent material with an indicator function according to claim 1, characterized in that another resin layer containing 5 to 80% zeolite by weight is superposed on the side of said resin layer at which said printed layer is disposed.

3. The moisture absorbent material with an indicator function according to claim 1, characterized in that the material has a barrier film superposed on at least one surface thereof.

4. The moisture absorbent material with an indicator function according to claim 3, characterized in that an ink of one color selected from white, black, red, blue, green, yellow, indigo, cyan and magenta or an ink of mixed colors selected therefrom is applied between said barrier film and said printed layer.

5. The moisture absorbent material with an indicator function according to claim 1, characterized in that an ink of one color selected from white, black, red, blue, green, yellow, indigo, cyan and magenta or an ink of mixed colors selected therefrom is applied to an opposite side of said resin layer which is provided with said printed layer.

6. The moisture absorbent material with an indicator function according to claim 1, characterized in that said resin layer exhibits light transmittance of 70% or more when moisture absorption of said resin layer reaches a saturation state.

7. The moisture absorbent material with an indicator function according to claim 1, characterized in that a film having a reflecting surface is superposed on at least one side of the moisture absorbent material.

8. The moisture absorbent material with an indicator function according to claim 1, characterized in that an ink used for said printed layer has a weight ratio of pigment or dye to resin within a range of 0.05 to 50 wt %.

9. The moisture absorbent material with an indicator function according to claim 8, characterized in that said printed layer has an ink film thickness of 0.3 to 100 μm.

10. The moisture absorbent material with an indicator function according to claim 1, characterized in that the material is so constructed that a printed pattern appears when a difference in optical density values between a whitish turbid state and a transparent state of said resin layer is rendered 0.05 or more.

11. A humidity indicator characterized in that a film using a zeolite-containing resin composition, a polyolefin film having a pattern printed thereon, and a film having a reflecting surface are laminated on one another, so that said pattern is rendered visible by utilizing a change of said film using the zeolite-containing resin composition from a whitish turbid state to a transparent state due to moisture absorption.

12. The humidity indicator according to claim 11, characterized in that a thermoplastic resin is superposed on said film using the zeolite-containing resin composition so as to regulate the rate of moisture absorption, to thereby control an increase rate of visibility of the pattern.

13. The humidity indicator according to claim 12, characterized in that a paint for enlarging an angle of visibility is applied to a surface of said thermoplastic resin.

14. The humidity indicator according to claim 12, characterized in that a film having a low refractive index is interposed between said polyolefin film having said pattern printed thereon and said film having said reflecting surface.

15. The humidity indicator according to claim 12, characterized in that a laminate constituted of said film using the zeolite-containing resin composition, said polyolefin film having said pattern printed thereon and said film having said reflecting surface is entirely interposed between films having a width larger than that of said film using the zeolite-containing resin composition and then subjected to a heat lamination process.

16. The humidity indicator according to claim 15, characterized in that said films used for the heat lamination have a water vapor transmission rate ranging from 0.1 to 100 g/m2/day.

17. The humidity indicator according to claim 15, characterized in that a color sample is printed on a film layer of said films used for the heat lamination so as to be able to judge a state of said pattern which appears with moisture absorption.

18. The humidity indicator according to claim 11, characterized in that said pattern is formed to have a difference in the print density of characters, symbols, lines or the like so that the degree of visibility may change, whereby the humidity of a space is clearly indicated.

19. A packaging bag characterized in that the bag is formed in a bag shape using a film provided on the whole of or on part of a face thereof with a moisture absorbent material with an indicator function according to claim 1.

* * * * *